（12) United States Patent
Liu

(10) Patent No.: US 8,513,468 B2
(45) Date of Patent: Aug. 20, 2013

(54) PROCESS FOR REMOVING DEGRADATION ACIDS FROM HYDROFORMYLATION REACTIONS

(75) Inventor: Yun-Shan Liu, The Woodlands, TX (US)

(73) Assignee: Eastman Chemical Company, Kingsport, TN (US)

( * ) Notice: Subject to any disclaimer, the term of this patent is extended or adjusted under 35 U.S.C. 154(b) by 91 days.

(21) Appl. No.: 12/982,177

(22) Filed: Dec. 30, 2010

(65) Prior Publication Data

US 2012/0172630 A1 Jul. 5, 2012

(51) Int. Cl.
*C07C 45/50* (2006.01)

(52) U.S. Cl.
USPC .................................................... 568/454

(58) Field of Classification Search
USPC ........................................................ 568/454
See application file for complete search history.

(56) References Cited

U.S. PATENT DOCUMENTS

| | | | |
|---|---|---|---|
| 3,239,566 A | 3/1966 | Slaugh et al. | |
| 3,284,350 A | 11/1966 | Williamson | |
| 3,527,809 A | 9/1970 | Pruett et al. | |
| 3,553,298 A | 1/1971 | Hodan et al. | |
| 3,959,132 A | 5/1976 | Singh | |
| 4,482,749 A | 11/1984 | Dennis et al. | |
| 4,496,768 A | 1/1985 | Dennis et al. | |
| 4,608,239 A | 8/1986 | Devon | |
| 4,717,775 A | 1/1988 | Billig et al. | |
| 4,789,753 A | 12/1988 | Billig et al. | |
| 4,879,008 A | 11/1989 | Puckette | |
| 4,912,155 A | 3/1990 | Burton | |
| 5,026,886 A | 6/1991 | Stavinoha et al. | |
| 5,041,228 A | 8/1991 | Herrmann et al. | |
| 5,180,854 A | 1/1993 | Abatjoglou et al. | |
| 5,208,362 A | 5/1993 | Glass et al. | |
| 5,230,806 A | 7/1993 | Fritz et al. | |
| 5,288,918 A | 2/1994 | Maher et al. | |
| 5,332,846 A | 7/1994 | Devon et al. | |
| 5,344,988 A | 9/1994 | Devon et al. | |
| 5,364,950 A * | 11/1994 | Babin et al. | 556/2 |
| 5,756,855 A | 5/1998 | Abatjoglou et al. | |
| 5,763,670 A | 6/1998 | Billig et al. | |
| 5,763,677 A * | 6/1998 | Bryant et al. | 568/454 |
| 5,789,625 A | 8/1998 | Bryant et al. | |
| 5,840,647 A | 11/1998 | Puckette et al. | |
| 5,917,095 A * | 6/1999 | Bryant et al. | 568/454 |
| 5,929,289 A | 7/1999 | Abatjoglou et al. | |
| 6,005,148 A | 12/1999 | Tanielyan et al. | |
| 6,232,263 B1 | 5/2001 | Tolleson et al. | |
| 6,482,324 B2 | 11/2002 | Kirkland et al. | |
| 6,693,219 B2 * | 2/2004 | Puckette et al. | 568/454 |
| 6,776,904 B2 | 8/2004 | Zhu et al. | |
| 6,846,960 B2 | 1/2005 | Tolleson et al. | |
| 6,946,580 B2 | 9/2005 | Banister et al. | |
| 6,995,292 B2 | 2/2006 | Tolleson et al. | |
| 7,041,623 B2 | 5/2006 | Kirkland et al. | |
| 7,063,784 B2 | 6/2006 | Jamalabadi et al. | |
| 7,128,884 B2 | 10/2006 | Kirkland et al. | |
| 7,301,054 B1 | 11/2007 | Puckette | |
| 7,420,093 B2 | 9/2008 | Puckette et al. | |
| 7,586,010 B2 | 9/2009 | Liu et al. | |
| 7,674,937 B2 | 3/2010 | Tolleson et al. | |
| 2002/0013399 A1 | 1/2002 | Groves | |
| 2002/0132119 A1 | 9/2002 | Kirkland et al. | |
| 2003/0018220 A1 | 1/2003 | Puckette et al. | |
| 2003/0136739 A1 | 7/2003 | Kirkland et al. | |
| 2004/0024344 A1 | 2/2004 | Trese et al. | |
| 2004/0089606 A1 | 5/2004 | Kirkland et al. | |
| 2004/0143140 A1 | 7/2004 | Sielcken et al. | |
| 2009/0171121 A1 | 7/2009 | Liu et al. | |
| 2010/0069679 A1 | 3/2010 | Puckette | |

FOREIGN PATENT DOCUMENTS

| | | |
|---|---|---|
| JP | 11189563 A | 7/1999 |
| WO | 01/051441 A1 | 7/2001 |
| WO | 02/098825 A2 | 12/2002 |
| WO | 03/061822 A2 | 7/2003 |

OTHER PUBLICATIONS

Bryant, David R.; "Chapter 2—Classical Homogeneous Catalyst Separation Technology" in Cole-Hamilton and Tooze, eds. Catalyst Separation, Recovery and Recycling—Chemistry and Process Design; 2006 Springer; pp. 9-37.
Klender, G. J.; "Chapter 26—Fluorophosphonites as Co-Stabilizers in Stabilization of Polyolefins" in Advanced in Chem. Series, No. 249 Polymer Durability; American Chemical Society 1993 meetings; published 1996, pp. 397-422.
Lewis, Richard J.; "Hawley's Condensed Chemical Dictionary"; Thirteenth Edition; p. 21, published Sep. 19, 1997.
Meyer, Thomas G. et al.; "Preparation and Single Crystal X-ray Diffraction Study of Some Fluorophosphites and Phosphite Esters"; Z. Naturforsch. vol. 48b; 1993, pp. 659-671.
Riesel, L. and Haenel, J.; "A Simple Synthesis of Fluoro(organyl)phosphanes"; Z. anorg. Allg. Chem. vol. 603; 1991; pp. 145-150.
Tullock, C. W. and Coffman, D. D.; "Synthesis of Fluorides by Metathesis with Sodium Fluoride"; Journal Org. Chem. vol. 25; 1960; pp. 2016-2019.
White, D. W. et al.; "Structural Implications of Nuclear Magnetic Resonance Studies on 1-R-1-Phospha-2,6-dioxacyclohexanes"; J. Am. Chem. Soc. vol. 92:24; 1970; pp. 7125-7135.
Notification of Transmittal of the International Search Report and the Written Opinion of the International Searching Authority, or the Declaration received in the corresponding International Application No. PCT/US2011/66348 dated Apr. 27, 2012.

* cited by examiner

*Primary Examiner* — Sikarl Witherspoon
(74) *Attorney, Agent, or Firm* — William K. McGreevey

(57) ABSTRACT

A process for removing degradation acids from a catalyst solution comprising a phosphorus-containing hydroformylation ligand used in a hydroformylation reaction is described. The process involves using a supported epoxy compound. Also described is a hydroformylation process that includes the degradation acids removal process.

25 Claims, No Drawings

PROCESS FOR REMOVING DEGRADATION ACIDS FROM HYDROFORMYLATION REACTIONS

FIELD OF THE INVENTION

This invention generally relates to a process for removing degradation acids that are formed during hydroformylation reactions using a catalyst containing a phosphorus-containing ligand. The invention also generally relates to a hydroformylation process that includes a process for removing degradation acids that are formed during hydroformylation reactions using a catalyst containing a phosphorus-containing ligand.

BACKGROUND OF THE INVENTION

The hydroformylation reaction, also known as the oxo reaction, is used extensively in commercial processes for the preparation of aldehydes by the reaction of one mole of an olefin with one mole each of hydrogen and carbon monoxide. One use of the reaction is in the preparation of normal- and iso-butyraldehyde from propylene. The normal- and iso-butyraldehydes obtained from propylene are in turn converted into many commercially-valuable chemical products such as, for example, n-butanol, 2-ethyl-hexanol, n-butyric acid, iso-butanol, neo-pentyl glycol, 2,2,4-trimethyl-1,3-pentanediol, the mono-isobutyrate and di-isobutyrate esters of 2,2,4-trimethyl-1,3-pentanediol.

In many cases, a catalyst system containing a Group VIII metal such as rhodium or cobalt is used to catalyze the oxo process. In addition, a phosphorus ligand such as halophosphites, phosphites, and phosphines can be used to regulate the activity of the Group VIII metal. However, many such phosphorus ligands can be degraded and thereby form acids during the oxo process because of degradation reactions involving the ligands. These degradation acids can cause cascading effects and catalyze further degradation of the ligands and lead to a significant loss of the phosphorus ligands.

Accordingly, there is a need in the art for a process for stabilizing phosphorus-containing catalyst systems against degradation in which minimal or no foreign components are to be introduced into the hydroformylation reactor.

The present invention solves this and other problems as will be apparent to those skilled in the art from reading the remainder of the description and the appended claims.

SUMMARY OF THE INVENTION

The present invention provides a process for removing at least one degradation acid from a catalyst solution containing at least one phosphorus-containing hydroformylation ligand, said process including contacting at least a portion of said catalyst solution with at least one supported epoxy compound at conditions effective to remove at least a portion of said at least one degradation acid from said catalyst solution.

The invention further provides a hydroformylation process that includes:
(a) contacting at least one olefin with carbon monoxide and hydrogen in the presence of a catalyst solution comprising at least one Group VIII metal and at least one phosphorus-containing hydroformylation ligand in a hydroformylation reactor at conditions effective to produce at least one aldehyde and a used catalyst solution containing at least one degradation acid; and
(b) contacting at least a portion of said used catalyst solution with at least one supported epoxy compound at conditions effective to remove at least a portion of said at least one degradation acid from said used catalyst solution.

In some embodiments, step (b) is carried out outside of the hydroformylation reactor. In some embodiments step (b) is conducted continuously while step (a) is being carried out, and the process further includes recycling at least a portion of the treated catalyst solution from step (b) back to step (a).

DETAILED DESCRIPTION OF THE INVENTION

Surprisingly, it has been discovered that a supported epoxy compound can be used to stabilize an oxo catalyst system by removing degradation acids generated during the oxo reaction. Thus, the present invention provides a process for removing degradation acids from a catalyst solution containing at least one phosphorus-containing compound used in a hydroformylation reaction. The process includes contacting at least a portion of the used catalyst solution with at least one supported epoxy compound at conditions effective to remove at least a portion of the degradation acids from the used catalyst solution.

The supported epoxy compound can be added directly to the catalyst solution in the hydroformylation reactor. However, it is also possible to contact the used catalyst solution or reaction medium, which contains the degradation acids, with the supported epoxy compound outside of the hydroformylation reactor. The separate contacting unit can be installed, for example, as a closed-loop catalyst treatment unit directly connected to the hydroformylation reactor or as a stand-alone unit downstream of one or more other process equipment for treating the used catalyst solution in an oxo process, thus reducing the potential for introducing foreign components into the oxo reactor.

As used herein, "supported epoxy compound" means a compound that contains one or more epoxide moieties and that is covalently bonded to a solid support such that it does not dissolve in the catalyst solution. In some embodiments, the supported epoxy compound have the structure of general formula (VII):

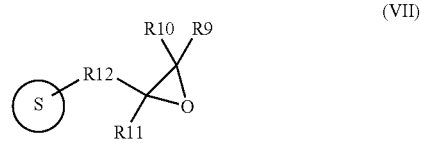

wherein Ⓢ is a solid support selected from silica gel, alumina, metal oxides, and cross-linked polymers such as polystyrene; R12 is a divalent bridging spacer group between the epoxy group and the support, the spacer being selected from the group consisting of substituted or unsubstituted alkyl, cycloalkyl, aryl, aralkyl, and alkaryl groups having up to about 40 carbon atoms; and R9, R10, and R11 are individually selected from hydrogen or substituents on the epoxy group that may contain up to 40 carbon atoms that are independently selected from the group consisting of substituted or unsubstituted alkyl, cycloalkyl, aryl, aralkyl, and alkaryl groups having up to about 40 carbon atoms. As used in reference to R9, R10, R11, and R12 the word "substituted" denotes the presence of one or more moieties that do not react with epoxide moieties under conditions in which the method is practiced. In some embodiments, "substituted" may denote the presence of one or more alkoxy groups, aryloxy groups, alkyl sulfide groups, amines having the formula —NR—, or silane groups having the formula —SiR'R"—, wherein each radical R, R', and R" individually represents alkyl, or aryl groups. In some embodiments, the compound is free of substituents selected from halogens, carboxyl moieties, amines, alcohols, thiols and sulfonic acids, each of which can react with epoxide moieties.

In some embodiments, the divalent spacer group R12 is bonded to solid support through covalent or ionic bonds. In some embodiments, the total carbon content of R12 is in the range of about 1 to 20 carbon atoms. In some embodiments, the total carbon content of R9 to R11 is in the range of about 0 to 40 carbon atoms.

In some embodiments, the epoxy group in the supported epoxy compound can include at least one ring in a cyclic structure formed by the combination of one of R9 and R10 groups with one of R11 and R12 groups. The cyclic structure can have a plurality of rings associated therewith, including bicyclo-, tricycle, tetracyclo-, and other n-cyclo groups.

In some embodiments, the supported epoxy compounds include SiliaBond® Glycidoxy or Si-Gly, which is a functionalized silica gel containing a glycidoxy group. SiliaBond® Glycidoxy is available from SiliCycle Inc. (Quebec, Canada) and has the following general formula (VIII):

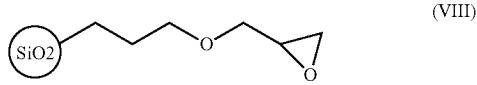

(VIII)

wherein SiO2 represents solid silica gel.

The loading of the epoxy component relative to the support can be a factor in efficiently carrying out the present invention. In some embodiments, the loading of the epoxy unit is in the range of 0.01 mmol of epoxy compound per gram of support to 10 mmol of epoxy compound per gram of support. In some embodiments, the loading of the epoxy unit is in the range of 0.1 mmol of epoxy compound per gram of support to 4.0 mmol epoxy compound per gram of support.

The bulk density of the supported epoxy compound can vary over a wide range. In some embodiments, the bulk density is in the range of 0.1 kg/L to 4.0 kg/L. In some embodiments, the bulk density is in the range of 0.2 kg/L to 2.0 kg/L.

The particle size of the supported epoxy compounds can vary over a wide range. In some embodiments, the particle size is in the range of from 0.1 to 100,000 micrometers (μm). In some embodiments, the particle size is in the range of from 10 to 1000 micrometers. In some embodiments, the particle size is in the range of from 50 to 1000 micrometers. In some embodiments, the particle size is in the range of from 250 to 1000 micrometers. Supports having a larger particle size can generate less pressure drop.

The shape of the supported epoxy compound particles can vary, so long as it does not create unacceptably high levels of pressure drop. For example, the shape can be spherical, non-spherical, or irregularly shaped. In the case of spherical particles, the size describes its diameter. In the case of non-spherical or irregularly shaped particles, the particle size describes the longest distance between two opposite points on the particle.

The particle size distribution of the supported epoxy compounds can also be a factor in efficiently practicing the invention. While it is difficult to specify the range of particle size distribution, generally, the narrower the particle size distribution, the better for the application.

The surface area of the supports can also be a factor in efficiently practicing the invention, since it determines the rate of interaction between the supported epoxy compounds and the degradation acids. Surface areas that are suitable for this application can vary over a wide range. In some embodiments, the surface area of the support is from 10 meters square per gram to 2000 meters square per gram. In some embodiments, the surface area of the support is from 50 meters square per gram to 500 meters square per gram.

The flow rate of the oxo catalyst solution through the supported epoxy compound bed should be sufficient to permit the epoxide moieties to interact and/or react with the degradation acids present. While the optimum flow rate can vary depending on the design of the contacting unit and the pressure, it is desirable that the flow rate is sufficient so that the concentration of the degradation acids be below 0.15 milliequivalents per liter after it passes through the supported epoxy compound bed.

The amount of supported epoxy compounds in accordance with the process of the invention should be sufficient to interact with the degradation acids that. In some embodiments, the quantity of epoxy compound is sufficient to maintain the concentration of degradation acids below the threshold level that causes rapid degradation of the ligand. In some embodiments, the quantity of supported epoxy compounds used in accordance with the invention is sufficient to maintain the concentration of degradation acids below 0.15 milliequivalents per liter after the catalyst solution passes through the epoxy compound contacting unit.

In some embodiments, the operating temperature of the epoxy compound contacting unit(s) can vary from 20° C. to 200° C. In some embodiments, the operating temperature is from 50° C. to 150° C.

In some embodiments, the operation pressure of the epoxy compound contacting unit(s) can vary from 1 psig to 1000 psig. In some embodiments, the operating pressure is from 5 psig to 700 psig.

Two or more of the epoxy compound contacting units may be used, and they can be installed either in series or in parallel as desired.

Any of the known solid/liquid processing equipment designs or configurations may be used in carrying out the process provided by the present invention. Thus, for example, a fixed-bed, a trickle-bed, or a fluidized-bed design may be used. In a fixed-bed mode of operation, the flow can be, for example, up flow or down flow mode. In any design, the contacting unit can have or not have recycling capability. It will be apparent to those skilled in the art that other contacting and/or recycling schemes may be used with this invention.

As used herein, "phosphorus-containing hydroformylation ligands" is any phosphorous compound useful as a ligand in a hydroformylation reaction. Some examples include halophosphites (e.g. fluorophosphites), phosphites, phosphinites, phosphonites, and phosphines. Some examples of phosphorous-containing hydroformylation ligands are described in U.S. Pat. Nos. 4,879,008, 5,026,886, 5,332,846, 5,344,988, 5,840,647, 6,232,263, 7,301,054, 7,420,093, 7,586,010, 7,674,937 and U.S. patent applications having publication numbers 2010/0069679, 2009/0171121 and 20090171122, all of the foregoing of which are incorporated by reference herein (except to the extent such disclosures contain definitions that would conflict with any definitions herein). In some embodiments, one or more phosphorus-containing hydroformylation ligand is selected from phosphines, phosphites, halophosphites, phosphonites, and phosphonites. In some embodiments, the at least one phosphorus-containing hydroformylation ligand is a fluorophosphite. For convenience, details of the present invention are, to some extent, described herein in particular as they relate to fluorophosphite-containing catalysts used in the hydroformylation of olefins to form aldehydes. However, the invention is not limited to the stabilization of fluorophosphite-containing catalysts utilized in olefin hydroformylation. Rather, it includes various other oxo catalyst systems such as phosphite-, phosphine-, phosphonite- and phosphinite-containing systems where there exists a need to reduce the degradation of phosphorus-containing hydroformylation ligands.

As used herein, a "degradation acid" is any acidic compound that is formed as a result of a degradation, decomposition or other reactions of phosphorus-containing hydroformylation ligands and that has an aqueous dissociation constant, pKa, that is less than 4.5. Some examples include phosphorous-containing acid compounds such as alkyl phosphonic acids (for example, those formed by the reactions described in U.S. Pat. No. 4,717,775 and in *Catalyst Separation, Recovery and Recycling-Chemistry and Process Design*, Edited by David J. Cole-Hamilton and Robert P. Tooze, Springer, 2006, Chapter 2, Page 25 to Page 27). Other examples include halide acids such as hydrofluoric acid (HF) (which can result, for example, from degradation of halophosphites such as fluorophosphites). A suitable method for measuring the concentration of the degradation acids in the oxo reaction mixture is disclosed in U.S. Pat. No. 6,693,219 (described as a method for detecting "strong acids"). In some embodiments, at least one degradation acid includes at least one phosphorus-containing acid compound. In some embodiments, at least one degradation acid includes at least one phosphorus-containing acid compounds and hydrofluoric acid.

The present invention further relates to a hydroformylation process that employs the degradation acids removal process described herein. In particular, the hydroformylation process includes:

(a) contacting at least one olefin with carbon monoxide and hydrogen in the presence of a catalyst solution comprising at least one Group VIII metal and at least one phosphorus-containing hydroformylation ligand in a hydroformylation reactor at conditions effective to produce at least one aldehyde and a used catalyst solution containing at least one degradation acid; and (b) contacting at least a portion of said used catalyst solution with at least one supported epoxy compound at conditions effective to remove at least a portion of said at least one degradation acid from said used catalyst solution. This contacting step (b) may include any of the embodiments and other aspects of the invention described above for processes for removing degradation acids from catalyst solutions.

Many hydroformylation catalyst systems include a combination of a transition metal selected from Group VIII transition metals and one or more phosphorus-containing hydroformylation ligands such as fluorophosphite compounds. The transition metal may be provided in any form of various metal compounds such as carboxylate salts of the transition metal. In some embodiments, the Group VIII metal is rhodium.

Examples of fluorophosphite ligands useful in the processes of the present invention are those having the general formula:

wherein R1 and R2 are hydrocarbyl radicals which contain a total of up to about 60 carbon atoms and wherein the ratio of gram moles of fluorophosphite ligand to gram atoms of transition metal is at least 1:1.

Fluorophosphite compounds function as effective ligands when used in combination with transition metals to form catalyst systems for the processes described herein. The hydrocarbyl groups represented by R1 and R2 may be the same or different, separate or combined, and are selected from unsubstituted or substituted alkyl, cycloalkyl, and aryl groups containing a total of up to about 60 carbon atoms. In some embodiments, the total carbon content of substituents R1 and R2 is in the range of about 2 to 35 carbon atoms. Examples of the alkyl groups which R1 and R2 separately or individually can represent include methyl, ethyl, butyl, pentyl, hexyl, 2-ethylhexyl, octyl, decyl, dodecyl, octadecyl, and various isomers thereof. The alkyl groups may be substituted, for example, with up to two substituents such as alkoxy, cycloalkoxy, formyl, alkanoyl, cycloalkyl, aryl, aryloxy, aroyl, carboxyl, carboxylate salts, alkoxycarbonyl, alkanoyloxy, cyano, sulfonic acid, sulfonate salts, and the like. Cyclopentyl, cyclohexyl and cycloheptyl are examples of the cycloalkyl groups that R1 and R2 can individually represent. The cycloalkyl groups may be substituted with alkyl or any of the substituents described with respect to the possible substituted alkyl groups. In some embodiments, the alkyl and cycloalkyl groups that R1 and R2 can individually represent are alkyl of up to about 8 carbon atoms, benzyl, cyclopentyl, cyclohexyl, or cycloheptyl.

Examples of the aryl groups that R1 and R2 can individually represent include carbocyclic aryl such as phenyl, naphthyl, anthracenyl, and substituted derivatives thereof. Examples of the carbocyclic aryl groups that R1 and R2 can individually represent are radicals having the formulas (II)-(IV) below:

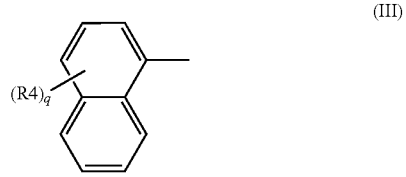

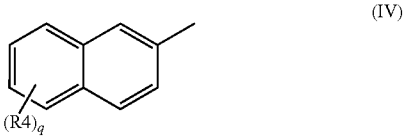

wherein R3 and R4 may represent one or more substituents independently selected from alkyl, alkoxy, halogen, cycloalkoxy, formyl, alkanoyl, cycloalkyl, aryl, aryloxy, aroyl, carboxyl, carboxylate salts, alkoxy-carbonyl, alkanoyloxy, cyano, sulfonic acid, sulfonate salts, and the like. In some embodiments, the alkyl moiety of the aforesaid alkyl, alkoxy, alkanoyl, alkoxycarbonyl, and alkanoyloxy groups in some embodiments contains up to about 8 carbon atoms. Although it is possible for p to represent 0 to 5 and for q to represent 0 to 7, the value of each of p and q in some embodiments will not exceed 2. In some embodiments R3 and R4 represent lower alkyl groups, i.e., straight-chain and branched-chain alkyl of up to about 4 carbon atoms, and p and q each represent 0, 1, or 2.

Alternatively, R1 and R2 in combination or collectively may represent a divalent hydrocarbylene group containing up to about 60 carbon atoms, for example from about 12 to 36 carbon atoms. Examples of such divalent groups include alkyl groups of about 2 to 12 carbon atoms, cyclohexyl, and divalent aryl moieties. Specific examples of the alkyl and cycloalkyl groups include ethylene, trimethylene, 1,3-butanediyl, 2,2-dimethyl-1,3-propanediyl, 1,1,2-triphenylethanediyl, 2,2,4-trimethyl-1,3-pentanediyl, 1,2-cyclohexylene, and the like.

In some embodiments, the fluorophosphite compounds are those wherein the fluorophosphite ester oxygen atoms are bonded directly to a ring carbon atom of a carboxylic, aromatic group, e.g., an aryl or arylene group represented by the following general formula (V):

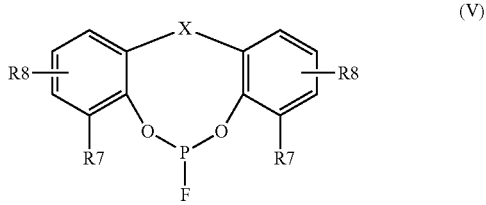

(V)

wherein R7 is independently selected from an alkyl of 3 to 8 carbon atoms; R8 is independently selected from hydrogen, an alkyl group having from 1 to 8 carbon atoms, or an alkyoxy group having 1 to 8 carbon atoms; and X is (i) a chemical bond directly between ring carbon atoms of each aromatic group; (ii) a hetero atom such as sulfur, oxygen or silicon; or (iii) a group having the formula (VI):

(VI)

wherein each of R5 and R6 is hydrogen or alkyl of 1 to 8 carbon atoms.

No special or unusual techniques are required for preparing the catalyst systems and solutions of the present invention, although in some embodiments all manipulations of the rhodium and fluorophosphite ligand components are carried out under an inert atmosphere, e.g., nitrogen, argon, and the like. The desired quantities of a suitable rhodium compound and ligand are charged to the reactor in a suitable solvent. The sequence in which the various catalyst components or reactants are charged to the reactor is not critical.

Rhodium compounds that may be used as a source of rhodium for the active catalyst include rhodium (II) or rhodium (III) salts of carboxylic acids, examples of which include di-rhodium tetraacetate dihydrate, rhodium(II) acetate, rhodium(II) isobutyrate, rhodium(II) 2-ethylhexanoate, rhodium(II) benzoate, and rhodium(II) octanoate. Also, rhodium carbonyl species such as $Rh_4(CO)_{12}$, $Rh_6(CO)_{16}$, and rhodium(I) acetylacetonate dicarbonyl may be suitable rhodium feeds. Additionally, rhodium organophosphine complexes such as tris(triphenylphosphine) rhodium carbonyl hydride may be used when the phosphine moieties of the complex fed are easily displaced by the phosphite ligands. Other rhodium sources include rhodium salts of strong mineral acids such as chlorides, bromides, nitrates, sulfates, phosphates, and the like.

The concentration of the rhodium and ligand in the hydroformylation solvent or reaction mixture is not critical for the successful operation of present invention. In some embodiments, a gram mole of ligand to gram atom of rhodium ratio of at least 1:1 is maintained in the reaction mixture. The absolute concentration of rhodium in the reaction mixture or solution may vary from 1 mg/liter up to 5000 mg/liter or more. When the hydroformylation process is operated in some embodiments, the concentration of rhodium in the reaction solution is in the range of about 20 to 300 mg/liter. Concentrations of rhodium lower than this range generally do not yield acceptable reaction rates with most olefin reactants and/or require reactor operating temperatures that are so high as to be detrimental to catalyst stability. Higher rhodium concentrations raise considerations around the cost of rhodium.

The selection of a suitable hydroformylation reaction solvent is not particularly limiting. Any solvent may be used that does not adversely affect the hydroformylation process and that is inert with respect to the catalyst, olefin, hydrogen, carbon monoxide, and supported epoxy compounds as well as the hydroformylation products. The supported epoxy compounds may or may not swell in such a solvent, but will not dissolve in the solvent. Inert solvents of this nature are well known to those skilled in the art and include such solvents as benzene, xylenes, toluene, saturated aliphatic hydrocarbon solvents, ethers, esters, ketones, alcohols, aldehydes, water, as well as various mixtures thereof.

The olefins that may be hydroformylated include aliphatic, including ethylenically unstaturated, low molecular weight polymers, alicyclic, aromatic and heterocyclic mono-, di- and tri-olefins containing up to about 40 carbon atoms. Examples of the aliphatic olefins that can be used in the hydroformylation process include ethylene, propylene, butene, pentene, hexene, octene, styrene, non-conjugated dienes such as 1,5-hexadiene, and blends of these olefins. Furthermore, the olefin may also be substituted with functional groups so long as they do not interfere with the hydroformylation reaction. Examples of substituted olefins include esters such as methyl acrylate and methyl oleate, alcohols such as allyl alcohol and 1-hydroxy-2,7-octadiene, and nitriles such as acrylonitrile.

The amount of olefin present in the reaction mixture can vary. For example, relatively high-boiling olefins such as 1-octene may function both as the olefin reactant and the process solvent. In the hydroformylation of a gaseous olefin feedstock such as propylene, the partial pressures in the vapor space in the reactor in some embodiments are in the range of about 0.07 to 35 bars absolute. In practice, the rate of reaction is favored by high concentrations of olefin in the reactor. In the hydroformylation of propylene, the partial pressure of propylene in some embodiments is greater than 1.4 bars, e.g., from about 1.4 to 10 bars absolute. In the case of ethylene hydroformylation, in some embodiments the partial pressure of ethylene in the reactor is greater than 0.14 bars absolute.

The hydroformylation reaction conditions used with the present invention may be any effective conditions, including those within the conventional hydroformylation conditions that are normally used. The process may be carried out at temperatures in the range of about 20° to 200° C. In some embodiments, the hydroformylation reaction temperatures are from 50° to 135° C. In some embodiments the reaction temperatures range from 75° to 125° C. Higher reactor temperatures can cause increased rates of catalyst decomposition while lower reactor temperatures result in relatively slow reaction rates. The total reaction pressure may range from about ambient or atmospheric up to 70 bars absolute (about 1000 psig). In some embodiments, the reaction pressure ranges from about 8 to 28 bars absolute (about 100 to 400 psig).

The hydrogen:carbon monoxide mole ratio in the reactor likewise may vary considerably, ranging from 10:1 to 1:10, and the sum of the absolute partial pressures of hydrogen and carbon monoxide may range from 0.3 to 36 bars absolute. Generally, the partial pressure of hydrogen and carbon monoxide in the reactor is maintained within the range of about 1.4 to 13.8 bars absolute (about 20 to 200 psia) for each gas. The partial pressure of carbon monoxide in the reactor is maintained within the range of about 1.4 to 13.8 bars absolute (about 20 to 200 psia) and is varied independently of the hydrogen partial pressure. The molar ratio of hydrogen to carbon monoxide can be varied widely within these partial pressure ranges for the hydrogen and carbon monoxide. The ratios of the hydrogen to carbon monoxide and the partial pressure of each in the synthesis gas (syn gas—carbon monoxide and hydrogen) can be readily changed by the addition of either hydrogen or carbon monoxide to the syn gas stream. It has been found that with the fluorophosphite ligands described herein, the ratio of linear to branched products can be varied widely by changing the partial pressures of the carbon monoxide in the reactor.

Any of the known hydroformylation reactor designs or configurations such as overflow reactors and vapor take-off reactors may be used in carrying out the process provided by the present invention. Thus, a gas-sparged, vapor take-off reactor design may be used. In this mode of operation, the catalyst which is dissolved in a high boiling organic solvent under pressure does not leave the reaction zone with the aldehyde product taken overhead by the unreacted gases. The overhead gases then are chilled in a vapor/liquid separator to liquefy the aldehyde products, and the gases can be recycled to the reactor. The liquid product is let down to atmospheric pressure for separation and purification by conventional technique. The process also may be practiced in a batchwise manner by contacting the olefin, hydrogen, and carbon monoxide with the catalyst in an autoclave.

A reactor design where catalyst and feedstock are pumped into a reactor and allowed to overflow with aldehyde products, i.e., liquid overflow reactor design, is also suitable. For example, high boiling aldehyde products such as nonyl aldehydes may be prepared in a continuous manner with the aldehyde product being removed from the reactor zone as a liquid in combination with the catalyst. The aldehyde product may be separated from the catalyst by conventional means such as by distillation or extraction, and the catalyst then recycled back to the reactor. Water soluble aldehyde products, such as hydroxy butyraldehyde products obtained by the hydroformylation of allyl alcohol, can be separated from the catalyst by extraction techniques. A trickle-bed reactor design is also suitable for this process. It will be apparent to those skilled in the art that other reactor schemes may be used with this invention.

The epoxy compound contacting step, as described herein, can be conducted continuously or intermittently while the hydroformylation reaction is carried out. It can also be carried out after the hydroformylation reaction has been terminated. The treated catalyst solution or any portion or component thereof can be recycled back, either stagewise or continuously, to the hydroformylation reactor for reuse.

This invention can be further illustrated by the following examples of preferred embodiments thereof, although it will be understood that these examples are included merely for purposes of illustration and are not intended to limit the scope of the invention. All percentages are by weight unless otherwise indicated.

EXAMPLES

Example 1

Model Experiment

This example illustrates that a silica gel supported epoxy compound can remove a degradation acid from a homogeneous solution.

A commercially available diphenylphosphinic acid was used in this example because it has a pKa similar to phosphorus acid and bears some structural similarity to the degradation acid α-hydroxyalkylphosphonic acid as disclosed by Bryant (*Catalyst Separation, Recovery and Recycling-Chemistry and Process Design*, Edited by David J. Cole-Hamilton and Robert P. Tooze, Springer, 2006, Chapter 2, Page 25 to Page 27). Thus, 2.2 grams of diphenylphosphinic acid was dissolved in 100 ml of di-2-ethylhexyl phthalate (DOP) under nitrogen at 90° C. and stirred for 20 min. The acidity of this solution was about 0.1M (or 100 milliequivalent per liter).

Then, 30 grams of glycidoxypropyl-functionalized silica gel (SiliaBond® Glycidoxy or Si-Gly, epoxide equivalent is about 1 mmol/gram, bulk density is 0.47 to 0.53 kg/L, particle size 40 to 60 μm, available from SiliCycle, Inc.) were added to the solution with agitation.

After 2 hours, an aliquot of 10 ml of the solution free of supported silica gel was taken, diluted with 95 ml of isopropyl alcohol and 5 ml of deionized water, and titrated with a Brinkman Titrator using 0.1013M NaOH.

The titration results showed that about 89.60% of diphenylphosphinic acid was no longer present.

After six hours, the titration showed that about 94% of the acid was no longer present in the solution.

The reaction was stopped after six hours. The SiliaBond® Glycidoxy was recovered through filtration and washed with acetone (200 ml). Then, the recovered SiliaBond® Glycidoxy was extracted with refluxing acetone using a Soxhlet extraction method for 8 hours and dried in air for 12 hours. This extraction process removes all physically adsorbed chemicals from the supported silica gel.

A SEM (Scan Electronic Microscopic) analysis showed that this recovered SiliaBond® Glycidoxy contains 0.72% of phosphorus on the surface. A fresh SiliaBond® Glycidoxy that had not been used as described above showed no evidence of phosphorus on surface.

Example 2

Comparative Experiment

This example illustrates that an unfunctionalized, regular silica gel does not provide the removal benefits of the epoxy-modified material.

Under the same reaction conditions as described in Example 1, 30 g of regular unfunctionalized silica gel (available from Aldrich, 70 to 230 mesh, BET surface area is about 500 m$^2$/g) was used to replace SiliaBond® Glycidoxy.

After 3.5 hrs at 90° C., titration showed less than 5% acid was no longer present in the solution.

After 6 hours, the silica gel was recovered, washed, and extracted with acetone in the same way as described in Example 1.

A SEM analysis showed no evidence of phosphorus present on the surface of this recovered silica gel.

Example 3

Model Experiment

This example illustrates that a polymer bounded epoxide resin can remove a degradation acid from a homogenous solution.

The same commercially available diphenylphosphinic acid was used in this example as in Example 1. 90 grams of poly(ethylene-co-glycidyl methacrylate) resin beads (available from Aldrich, containing about 8% of glycidyl methacrylate by weight, epoxide equivalent is about 0.05 mmol/gram) were soaked in 100 ml of di-2-ethylhexyl phthalate (DOP) in a flask and stirred for 48 hours at ambient temperature and then for another 48 hours at 90° C. with agitation.

2.2 grams of diphenylphosphinic acid was then added to the flask under nitrogen. The reaction temperature of the solution was maintained at 90° C. and agitated. The initial acidity of this solution was about 0.1M (or 100 milliequivalent per liter).

After 3 hours, an aliquot of 10 ml of the solution free of polymer beads was taken, diluted with 95 ml of isopropyl alcohol and 5 ml of deionized water, and titrated with a Brinkman Titrator using 0.1011M NaOH.

The results showed that about 30% of diphenylphosphinic acid was not long present in the solution.

After 48 hours, the titration showed that about 80% of the acid was no longer present in the solution.

Example 4

This example illustrates a fixed bed set-up using a supported epoxide-silica gel to remove degradation acids from a hydroformylation catalyst solution.

A used catalyst solution was taken from a hydroformylation reactor in which a fluorophosphite was used as the ligand.

The used catalyst solution contained 20 to 500 ppm of hydrofluoric acid, 0.01 to 1.0 milliequivalent/liter of phosphorous-containing degradation acids, about 0.5 to 1.5% of the fluorophosphite ligand, various amounts of butyraldehydes (10% to 60%), Texanol® (2,2,4-trimethyl-1,3-pentanediol monobutyrate solvent, 10% to 60%), and a certain amount of heavy components (1% to 20%).

The degradation acid removal process of the aged catalyst solution was carried out in a hot-tub, fixed-bed reactor composed of a vertically arranged stainless steel pipe having a 12.7 mm (½ inch) inside diameter and a length of 762 mm (30 inches). The reactor was encased in an external jacket that was connected to a hot oil machine. The reactor had a filter-like, loose fitting stainless steel net near the very bottom of the reactor for holding all solid components. The reactor temperature was controlled by the external hot oil bath. The bottom of the reactor has a pressure tubing connection that was connected to a cross. One of the connections to the cross was used for sampling purposes or for emergency releases, another led to the product collection unit. A pressure gauge, a release valve, and a back-pressure regulator were provided between the production collection unit and the cross. The production collection unit was connected to a nitrogen inlet, which protected the product from oxygen. The top of the reactor had a pressure tubing connection that was connected to the feed tank. The feed tank was protected under nitrogen atmosphere. A feed pump that could operate up to 200 psig was configured to feed the used catalyst solution.

In order to achieve a leak-free system, the bottom layer of the reactor was filled with glass wool about one inch thick. On top of the glass wool was a layer of sea sand about two inches thick. Then, the SiliaBond® Glycidoxy was added to the reactor, about 11 inches thick. Above the SiliaBond® Glycidoxy was a layer of marble chips about two inches thick.

In this experiment, 15 grams of SiliaBond® Glycidoxy (particle size 60 to 200 μm, epoxide equivalent is about 1 mmol/gram, bulk density is 0.47 to 0.53 kg/L) was used. The reactor temperature was set at 90° C. by the external oil bath, and the catalyst solution was fed at the rate of 100 ml/hour. The product generated during the first two hours of operation was discarded. Then, a total of 400 ml of treated catalyst solution was collected during the following 4 hours of operation and analyzed.

Analysis showed that this treated catalyst solution contained no detectable amount of degradation acids and the rhodium concentration remained unchanged.

The feed rate of the catalyst solution was then increased to 200 ml/hour.

Another 400 ml of treated catalyst solution were collected and analyzed. The results showed no detectable amount of degradation acids and the rhodium concentration remained unchanged.

The results are listed in Table 1.

TABLE 1

Results of SiliaBond ® Glycidoxy Treatment

| Substance | Before Treatment | After Treatment at 100 ml/hr, 90° C. | After Treatment at 200 ml/hr, 90° C. |
|---|---|---|---|
| P-Containing Degradation acids | 0.246 meq/L | 0.0 meq/L | 0.0 meq/L |
| HF | 181.0 ppm | 78.67 ppm | 116.45 ppm |

The invention has been described in detail with particular reference to preferred embodiments thereof, but it will be understood that variations and modifications can be effected within the spirit and scope of the invention.

What is claimed is:

1. A process for removing at least one degradation acids from a catalyst solution comprising at least one phosphorus-containing hydroformylation ligand, said process comprising contacting at least a portion of said catalyst solution with at least one supported epoxy compound at conditions effective to remove at least a portion of said at least one degradation acid from said catalyst solution.

2. The process according to claim 1, wherein said at least one phosphorus-containing hydroformylation ligand is selected from phosphines, phosphites, halophosphites, phosphonites, and phosphinites.

3. The process according to claim 2, wherein said at least one degradation acid comprises at least one phosphorus-containing acid compound.

4. The process according to claim 1, wherein said at least one phosphorus-containing hydroformylation ligand comprises a fluorophosphite.

5. The process according to claim 4, wherein said at least one degradation acid comprises at least one phosphorus-containing acid compounds and hydrofluoric acid.

6. The process according to claim 1, wherein said at least one supported epoxy compound comprises a compound having the formula (VII):

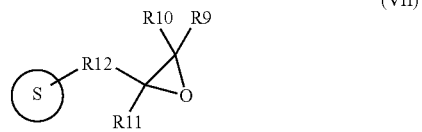

wherein
- Ⓢ is a solid support selected from silica gel, alumina, metal oxide, and cross-linked polymer; and
- R9, R10, and R11 are independently selected from the group consisting of hydrogen and substituted or unsubstituted alkyl, cycloalkyl, aryl, aralkyl, and alkaryl groups having up to about 40 carbon atoms, and in which the substitutions, if present, are selected from —O—, —S—, —NR—, —SiR'R"—, and —CO—, wherein each radical R, R', and R" represents alkyl, or aryl; and
- R12 is selected from the group consisting of substituted or unsubstituted alkyl, cycloalkyl, aryl, aralkyl, and alkaryl groups having up to about 40 carbon atoms, and in which the substitutions, if present, are selected from —O—, —S—, —NR—, —SiR'R"—, and —CO—, wherein each radical R, R', and R" represents alkyl, or aryl.

7. The process according to claim 1, wherein said at least one supported epoxy compound comprises a compound having the formula (VIII):

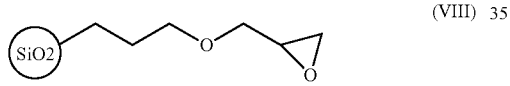

wherein SiO2 represents silica gel.

8. The process according to claim 1, wherein said at least one supported epoxy compound comprises a compound containing 0.1 to 4.0 mmol of epoxy compound per gram of support.

9. The process according to claim 1, wherein said at least one supported epoxy compound comprises a support having a surface area ranging from 50 to 500 $m^2/g$.

10. The process according to claim 1, wherein said contacting step is carried out at a temperature of 50 to 150° C. and a pressure of 5 to 700 psig.

11. The process according to claim 1, wherein said at least one supported epoxy compound comprises a compound having a particle size ranging from 250 to 1000 micrometers.

12. A hydroformylation process, which comprises:
(a) contacting at least one olefin with carbon monoxide and hydrogen in the presence of a catalyst solution comprising at least one Group VIII metal and at least one phosphorus-containing hydroformylation ligand in a hydroformylation reactor at conditions effective to produce at least one aldehyde and a used catalyst solution comprising at least one degradation acid; and
(b) contacting at least a portion of said used catalyst solution with at least one supported epoxy compound at conditions effective to remove at least a portion of said at least one degradation acid from said used catalyst solution.

13. The process according to claim 12, wherein said at least one phosphorus-containing hydroformylation ligand is selected from phosphines, phosphites, halophosphites, phosphonites, and phosphinites.

14. The process according to claim 13, wherein said at least one degradation acid comprises at least one phosphorus-containing acid compound.

15. The process according to claim 12, wherein said at least one phosphorus-containing hydroformylation ligand comprises a fluorophosphite.

16. The process according to claim 15, wherein said at least on degradation acid comprises at least one phosphorus-containing acid compounds and hydrofluoric acid.

17. The process according to claim 12, wherein said at least one supported epoxy compound comprises a compound having the formula (VII):

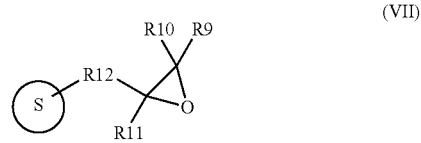

wherein
- Ⓢ is a solid support selected from silica gel, alumina, metal oxide, and cross-linked polymer; and
- R9, R10, and R11 are independently selected from the group consisting of hydrogen and substituted or unsubstituted alkyl, cycloalkyl, aryl, aralkyl, and alkaryl groups having up to about 40 carbon atoms, and in which the substitutions, if present, are selected from —O—, —S—, —NR—, —SiR'R"—, and —CO—, wherein each radical R, R', and R" represents alkyl, or aryl; and
- R12 is selected from the group consisting of substituted or unsubstituted alkyl, cycloalkyl, aryl, aralkyl, and alkaryl groups having up to about 40 carbon atoms, and in which the substitutions, if present, are selected from —O—, —S—, —NR—, —SiR'R"—, and —CO—, wherein each radical R, R', and R" represents alkyl, or aryl.

18. The process according to claim 17, wherein said at least one supported epoxy compound comprises a compound having the formula (VIII):

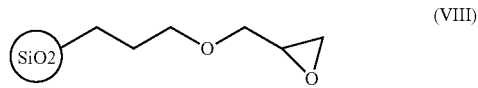

wherein SiO2 represents silica gel.

19. The process according to claim 12, wherein said at least one supported epoxy compound comprises a compound containing 0.1 to 4.0 mmol of epoxy compound per gram of support.

20. The process according to claim 12, wherein said at least one supported epoxy compound comprises a support having a surface area ranging from 50 to 500 $m^2/g$.

21. The process according to claim 12, wherein step (b) is carried out at a temperature of 50 to 150° C. and a pressure of 5 to 700 psig.

22. The process according to claim 12, wherein said at least one supported epoxy compound comprises a compound containing having a particle size ranging from 250 to 1000 micrometers.

23. The process according to claim 12, wherein step (b) is carried out outside of the hydroformylation reactor.

24. The process according to claim 23, wherein step (b) is conducted continuously while step (a) is being carried out, and which further comprises recycling at least a portion of the treated catalyst solution from step (b) back to step (a).

25. The process according to claim 23, wherein step (b) is carried out intermittently while step (a) is being carried out, and which further comprises recycling at least a portion of the treated catalyst solution from step (b) back to step (a).

* * * * *

UNITED STATES PATENT AND TRADEMARK OFFICE
CERTIFICATE OF CORRECTION

PATENT NO. : 8,513,468 B2
APPLICATION NO. : 12/982177
DATED : August 20, 2013
INVENTOR(S) : Yun-Shan Liu Page 1 of 1

It is certified that error appears in the above-identified patent and that said Letters Patent is hereby corrected as shown below:

In the claims

Column 14, Line 13, Claim 16 "on" should read --one--.

Signed and Sealed this
Nineteenth Day of July, 2016

Michelle K. Lee
*Director of the United States Patent and Trademark Office*